United States Patent [19]

Hirao et al.

[11] Patent Number: 4,914,424
[45] Date of Patent: Apr. 3, 1990

[54] OXYGEN CONCENTRATION MONITOR USING GALVANIC CELL TYPE OXYGEN SENSOR

[75] Inventors: Atsushi Hirao; Yasufumi Fukao, both of Kyoto, Japan

[73] Assignee: Japan Storage Battery Company, Limited, Kyoto, Japan

[21] Appl. No.: 163,334

[22] Filed: Mar. 2, 1988

[30] Foreign Application Priority Data

| Mar. 2, 1987 | [JP] | Japan | 62-48492 |
| Mar. 2, 1987 | [JP] | Japan | 62-48493 |
| Mar. 2, 1987 | [JP] | Japan | 62-48494 |
| Mar. 2, 1987 | [JP] | Japan | 62-48495 |

[51] Int. Cl.$^4$ ............................................. G08B 17/10
[52] U.S. Cl. ..................................... 340/632; 73/1 G; 73/23; 340/633
[58] Field of Search ....................... 340/632, 633, 634; 73/25, 26, 27 R, 27 A, 1 G

[56] References Cited

U.S. PATENT DOCUMENTS

| 4,431,004 | 2/1984 | Bessman | 128/635 |
| 4,495,051 | 1/1985 | Fujita et al. | 204/415 |
| 4,550,726 | 11/1985 | McEwen | 128/202.22 |
| 4,602,653 | 7/1986 | Ruiz-Vela | 128/204.22 |

Primary Examiner—Joseph A. Orsino
Assistant Examiner—Jill Jackson
Attorney, Agent, or Firm—Sughrue, Mion, Zinn, Macpeak & Seas

[57] ABSTRACT

The invention discloses an oxygen concentration monitor using a Galvanic cell type oxygen sensor. An automatic calibration circuit always calibrates the maximum output of the sensor as the value corresponding to an oxygen concentration of 21%, based on the fact that the oxygen concentration in a fresh air never exceeds 21%.

6 Claims, 5 Drawing Sheets

4,914,424

OXYGEN CONCENTRATION MONITOR USING GALVANIC CELL TYPE OXYGEN SENSOR

FIELD OF THE INVENTION

The present invention relates to an oxygen concentration monitor for monitoring oxygen concentration in a room and for actuating an alarm when the oxygen concentration in the room becomes lower than a predetermined concentration, so that a serious accident due to lack of oxygen may be prevented.

BACKGROUND OF THE INVENTION

A Galvanic cell type oxygen sensor is generally utilized for detecting an oxygen concentration. The principle of the sensor is based on the fact that a current flowing in a lead-oxygen cell is proportional to the oxygen concentration. When the current from the sensor is fed to a resistor connected to it, a voltage varying linearly with the oxygen concentration appears at both ends of the resistor, as shown in FIG. 1. The oxygen concentration monitor of the present invention is designed to check an output of the Galvanic cell type oxygen sensor and monitor whether or not the oxygen concentration has become abnormal.

However, this sensor is defective in that slight differences in electrode reaction areas occurring in producing the sensor cause differences in the outputs of the sensors. As a result, fluctuations occur in the outputs even when the sensors are produced in the same lot. As a result, the sensors are not usually replaceable for one another. Furthermore, the outputs of the sensors tend to decrease gradually as time proceeds. Accordingly, it is necessary to incorporate a calibration circuit for calibrating the fluctuation and the change with time of the output characteristics of the sensor into the oxygen concentration monitor.

Although the calibration of the differences in outputs of the sensors can be conducted by a manufacturer of the monitor, the calibration of the change with time has to be conducted by a user. Therefore, the calibration is required to be conducted as simply as possible.

Thus, various circuits have been proposed and practically used which allow a user to simply conduct such calibration.

One of the circuits is characterized by first storing an output of the sensor in fresh air as a value corresponding to the oxygen concentration of 21%, and by setting a reference value to a value obtained by subtracting a proportion of the stored output. If the oxygen concentration in the room to be measured is decreased, and the output of the sensor becomes lower than the reference value, an alarm is activated.

In the circuit as mentioned above, a calibration timing or the time for storing the fresh-air output of the sensor may be at the same time when a replaced sensor is restarted, or may be at an arbitrary time for calibration against the change in the output with elapsed time. That is, a user can calibrate by giving a contact signal to the circuit manually at the above-mentioned timing.

However, although the prior art circuits allow the user to simply conduct the calibration, they still exhibit the problem that proper calibration timing cannot be guaranteed. Because the user cannot check whether or not the oxygen concentration at the calibration time is truly 21%, the user might actually calibrate at lower oxygen concentration than 21%.

If the circuit is installed so as to indicate the alarm when the output of the sensor is decreased to the value corresponding to the proportion of 18/21 with reference to the stored value, the alarm is indicated at an oxygen concentration of 18% in a normal use. However, if the user calibrates erroneously at the oxygen concentration of 19%, the alarm is not indicated until the oxygen concentration reaches 16.3% (19×18/21).

Thus, if the calibration is erroneously conducted, the function of the alarm is insignificant. Additionally, if the user relies on such a monitor, he may be endangered.

SUMMARY OF THE INVENTION

The present invention provides an oxygen concentration monitor using the Galvanic cell type oxygen sensor which has as automatic calibration circuit that always calibrates the maximum output of the sensor as the value corresponding to the oxygen concentration of 21%, based on the fact that the oxygen concentration in fresh air never exceeds 21%. According to the invention, the erroneous calibration of the oxygen sensor will be eliminated.

DETAILED DESCRIPTION OF THE INVENTION

Acording to the present invention, an output voltage of the sensor is amplified to correspond to a reference voltage of a comparator since the output voltage in itself is too low to compare with the reference voltage. In this case, if the output characteristics of the sensors are uniform, it is sufficient to make an amplifier gain constant. However, since the output characteristics of the sensors are actually differenct, it is necessary to calibrate such differences in the output characteristics of the sensors before the output voltage is applied to the comparator.

The present invention includes three methods for calibrating the differences in output characteristics of the sensors. The first method will be described in Example I, wherein the output voltage of the sensor is amplified by an operational amplifier with a constant amplifier gain, and is then calibrated by varying an attenuation quantity by means of an attenuator. The second method will be described in Example II, wherein the output voltage of the sensor is applied to the attenuator to vary the attenuation quantity, and such a varied voltage is applied to the operational amplifier. Finally, the third method will be described in Example III, wherein the amplifier gain of the operational amplifier is regulated to calibrate the differences in output characteristics of the sensors.

EXAMPLE I

Figure 1:
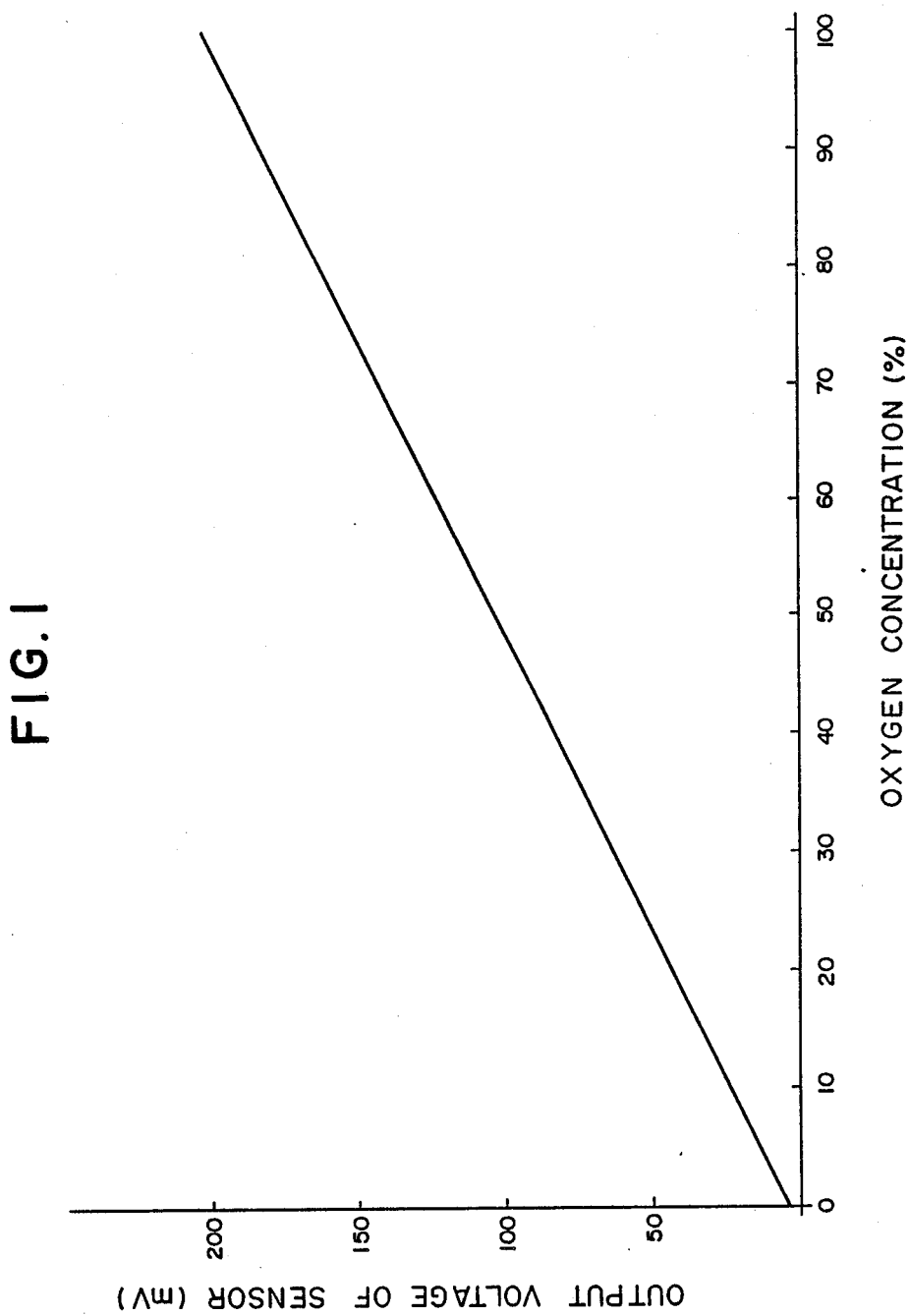
FIG. 1 is a graph showing the relation between the oxygen concentration and the output of the Galvanic cell type oxygen sensor.
Figure 2:
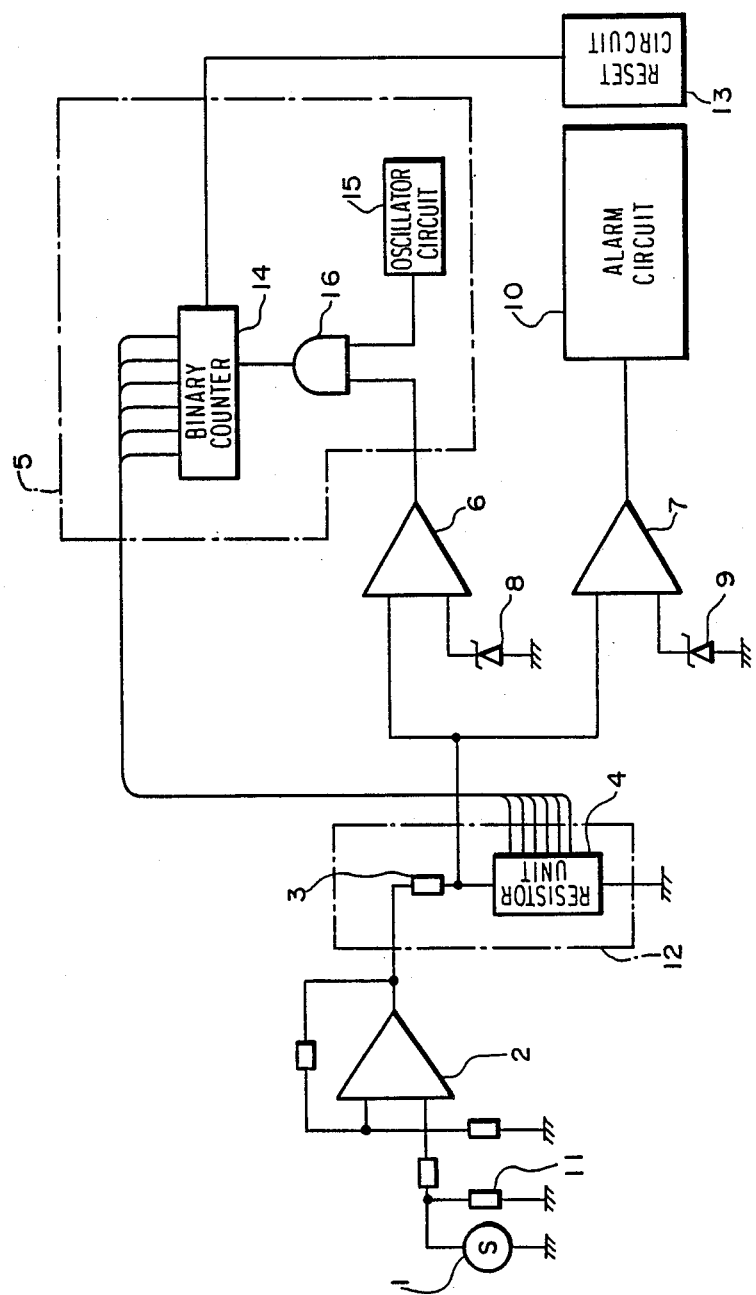
FIG. 2 is a block diagram of a first preferred embodiment of the automatic calibrating oxygen concentration monitor according to the present invention, wherein an attenuator for varying an attenuation quantity is provided on the output side of an amplifier.

FIG. 2 shows an electrical circuit of the oxygen concentration monitor in Example I. As a Galvanic cell type oxygen sensor 1 generates a current output, a resistor 11 is connected to the sensor 1 so as to convert the current output to a voltage output. The voltage at both ends of the resistor 11 varies in proportion to the oxygen concentration. Then, the voltage is output is fed to an operational amplifier 2 to amplify the same. Reference numeral 3 designates a resistor, and reference numeral 4 designates a resistor unit composed of switches and resistors. The resistor 3 and the resistor unit 4 are connected in series to construct an attenuator 12. An output signal from the attenuator 12 is fed from a connection point between the resistor 3 and the resistor unit 4.

Figure 3:
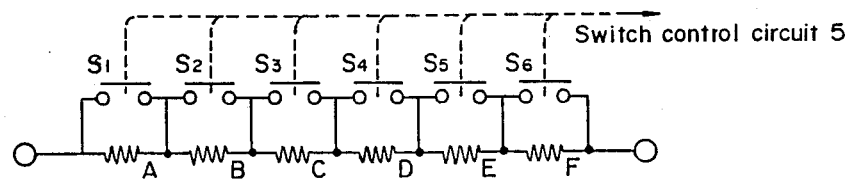
FIG. 3 is an example of a resistor unit employed in the present invention, which unit is composed of a plurality of assemblies connected in series, each assembly being composed of a resistor and a switch connected in parallel.
Figure 4:
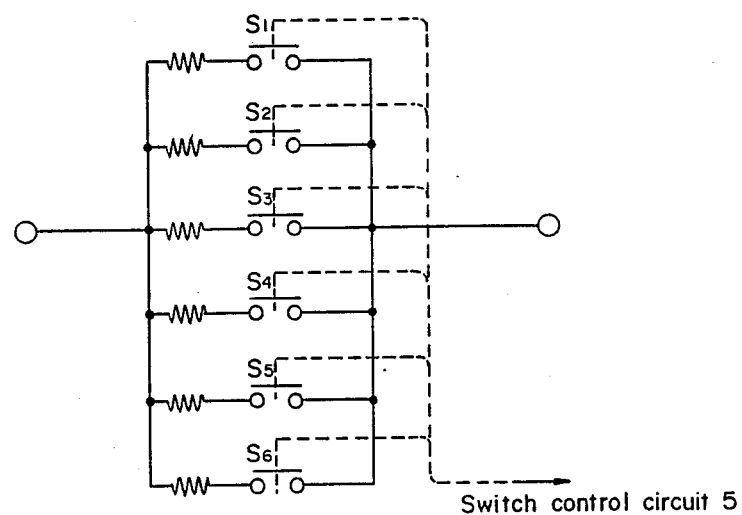
FIG. 4 is another example of the resistor unit composed of a plurality of assemblies connected in parallel, each assembly being composed of a resistor and a switch connected in series.
Figure 5:
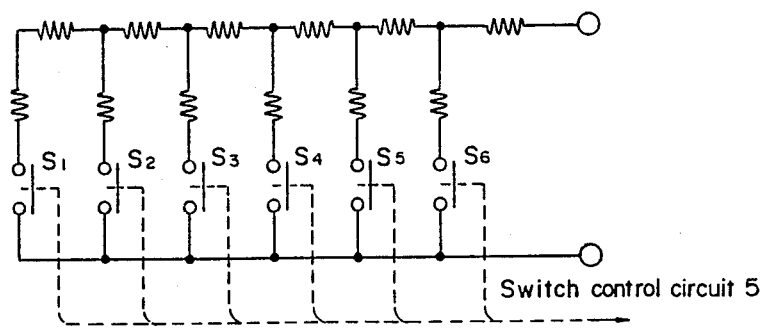
FIG. 5 is a further example of the resistor unit composed of a resistor ladder including a plurality of resistors connected in series and parallel and a plurality of switches each connected in series with each of the output terminals of the resistor ladder.

FIG. 3 shows an example of a circuit of the resistor unit 4. The circuit is formed by a plurality of assemblies connected in series, each assembly being composed of a resistor and a switch connected in parallel. FIG. 4 shows another example wherein the circuit is formed by a plurality of assemblies connected in parallel, each assembly being composed of a resistor and a switch connected in series. FIG. 5 shows a further example wherein the circuit is formed by a resistor ladder composed of a plurality of resistors and switches in combination like a ladder. The present inventione employs such a resistor unit constituting the attenuator 12, and enables automatic calibration as described below.

The switches of the resistor unit 4 are operated in such a manner that the resistance of the resistor unit 4 is gradually changed from a large value to a small value.

Next will be described a method for changing the resistance of the resistor unit 4 with reference to FIG. 3. The resistor unit 4 is composed of six resistors A–F and six switches $S_1$–$S_6$. The resistance of the resistor B is twice that of the resistor A. The resistance of the resistor C is twice that of the resistor B. The resistance of the resistor D is twice that of the resistor C. The resistance of the resistor E is twice that of the resistor D. The resistance of the resistor F is twice that of the resistor E.

Assuming that the resistance of the resistor A is $K\Omega$, the resistance of the resistor B becomes 2 $K\Omega$. Similarly, the resistances of the resistors C, D, E and F become 4, 8, 16 and 32 $K\Omega$, respectively. When all of the switches $S_1$–$S_6$ connected in parallel to the respective resistors are open, the resistance of the resistor unit 4 becomes 63 $K\Omega$.

At first, all of the switches S1–S6 are open. Then the switch S1, connected in parallel to the resistor A, is closed. As a result, the resistance of the resistor unit 4 becomes 62 $K\Omega$. Subsequently, when the switch S1 is opened and the switch $S_2$ is closed, the resistance of the resistor unit 4 becomes 61 $K\Omega$. Then, when the switch $S_2$ remains closed, and the switch S1 is closed, the resistance of the resistor unit 4 becomes 60 $K\Omega$.

That is to say, the resistance of the resistor unit 4 can be gradually changed from a large value to a small value by sequentially closing and opening the switches connected to the resistors from a small weight according to a binary code. As the resistance of the resistor 3 is fixed, an output signal from the attenuator 12 is gradually attenuated according to the binary code.

A switch control circuit 5 for controlling the opening and closing operation of the switches $S_1$–$S_6$ utilizes an output from a binary counter 14. The switch control circuit 5 comprises the binary counter 14, an oscillator circuit 15 and a gate circuit 16. A clock generated from the oscillator circuit 15 is inputted through the gate to the binary counter 14. Every time one clock pulse inputted, the binary code is changed by one, which is utilized as an opening and closing signal. The switch control circuit 5 also functions to control whether or not the clock generated from the oscillator circuit 15 should be passed through the gate according to an output from a comparator 6. In addition, switch control circuit 5 instructs whether an output from the binary counter 14 should be advanced or maintained.

The output terminal of the attenuator 12 is connected to the comparator 6 and a comparator 7. The comparator 6 compares an output signal from the attenuator 12 with a reference voltage 8. When the output signal from the attenuator 12 is greater that the reference voltage 8, the comparator 6 feeds a signal to the gate of the switch control circuit 5 so as to advance the count on the binary counter 14 in the switch control circuit 5. This reduces the amplifier gain of the operational amplifier 2. In contrast, when the output signal from the attenuator 12 becomes smaller than the reference voltage 8, the comparator 6 feeds a signal to the gate of the switch control circuit 5 so as to maintain the count on the binary counter 14. The comparator 7 compares the output signal from the attenuator 12 with a reference voltage 9. When the output signal from the attenuator 12 becomes smaller than the reference voltage 9, the comparator 7 feeds a signal to an alarm circuit 10 to activate an alarm to signal the reduction in the oxygen concentration.

Further, to compensate for the fact that the output of the sensor is gradually decreased as time proceeds, the maximum output of the sensor as stored is accordingly decreased, and the stored count value of the binary counter 14 is cleared periodically or upon application of power. For example, a reset switch is provided at a reset terminal of the binary counter 14. Alternatively, a reset circuit 13 such as a power on reset circuit for resetting the binary counter is provided at the reset terminal of the binary counter.

EXAMPLE II

Figure 6:
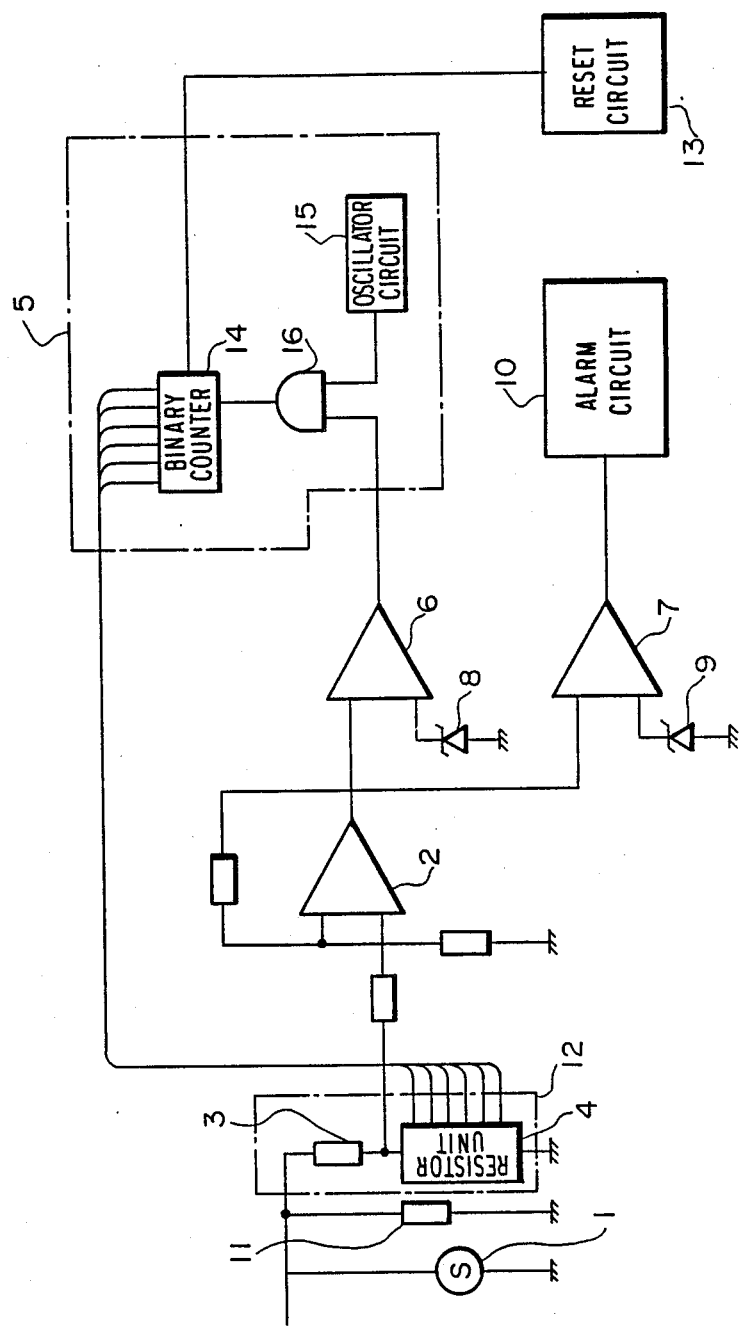
FIG. 6 is a second embodiment of the present invention, wherein the attenuator is provided on the input side of the amplifier.

In example I, the differences in output characteristics of the sensors are calibrated by varying the amount of attenuation of the attenuator provided on the output side of the amplifier. To the contrary, in Example II, the differences in output characteristics of the sensors are calibrated by varying the attenuation quantitiy of the attenuator provided on the input side of the amplifier. FIG. 6 shows the circuit diagram of Example II.

Similar to Example I, the differences in output characteristics of the sensors are absorbed at the operational amplifier. The output of the sensor 1 is inputted through the attenuator 12 to the operational amplifier 2. Then, the output amplified by the operational amplifier 2 is fed to the comparator 6, and is compared with the reference voltage 8. When the output is higher than the reference voltage 8, the count value of the binary counter 14 in the switch control circuit 5 is advanced to reduce the resistance of the resistor unit 4, and to thereby increase the amount of attenuation of the attenuator 12. As a result, an input voltage of the operational amplifier 2 is reduced. When an input signal of the comparator 6 becomes smaller than the reference voltage 8, the count value of the binary counter 14 in the switch control circuit 5 is maintained, and accordingly the resistance of the resistor unit 4 is maintained. A method for varying the resistance of the resistor unit 4 is quite similar to that in Example I. Further, an alarm circuit and a reset circuit are also similar to those in Example I.

EXAMPLE III

Figure 7:
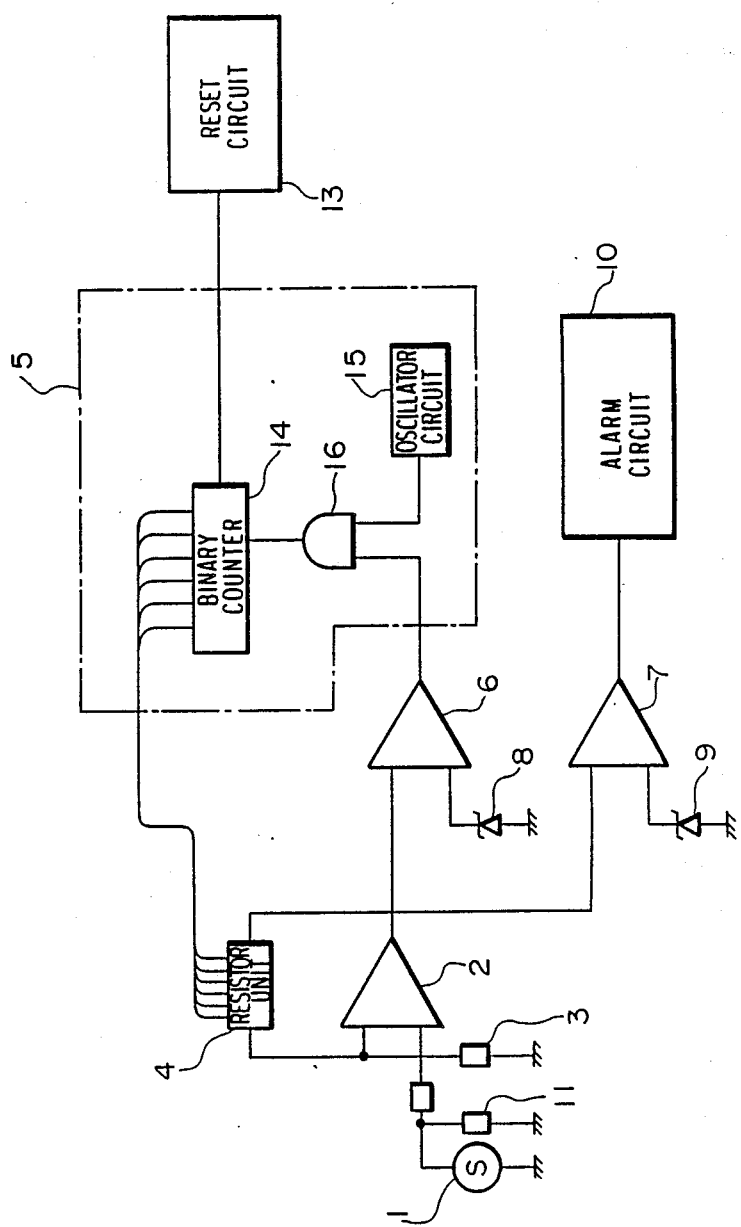
FIG. 7 is a third embodiment of the present invention, wherein the resistor unit is provided for a feedback resistor of the amplifier, so as to vary an amplifier gain.

In Examples I and II as mentioned above, the differences in output characteristics of the sensors are calibrated by varying the amount of attenuation of the attenuator provided on the output side of the amplifier or on the input side thereof. In Example III to now be described, the differences in output characteristics of the sensors are calibrated by varying the amplifier gain of the amplifier. FIG. 7 shows the circuit diagram of Example III.

The output of the sensor 1 is fed to the operational amplifier 2, and is amplified thereby. The amplified output from the amplifier 2 is fed to the comparator 6, and is compared with the reference voltage 8 by the comparator 6. When the output is higher than the reference voltage 8, the count value of the binary counter 14 in the switch control circuit 5 is advanced to reduce the resistance of the resistor unit 4. The reduction in resistance of the resistor unit 4 results in a decrease in amplifier gain of the operational amplifier 2. Accordingly, the output from the operational amplifier 2 is also reduced. That is, the input to the comparator reaches a value lower than the reference voltage 8. At this time, the count value of the binary counter 14 in the switch control circuit 5 is maintained, and accordingly the resistance of the resistor unit 4 is also maintained.

A method for varying the resistance of the resistor unit 4 in Example III is also quite similar to that in Example I. Further, an alarm circuit and a reset circuit are also similar to those in Example I.

As descibed above, the calibration circuit of the present invention is designed to regulate the amount of attenuation or the degree of amplification when the output of the Galvanic cell type oxygen sensor varies. This is accomplished by using the fact that the maximum output of the sensor corresponds to an oxygen concentration of 21%. Accordingly, a user need not account for the oxygen concentration in the atmosphere. Instead it it only necessary to switch on a power source. Thereafter, the monitor periodically carries out the automatic calibration with reference to an oxygen concentration of 21% in the atmosphere.

What is claimed is:

1. An oxygen concentration monitor comprising:
   a Galvanic cell type oxygen sensor;
   an operational amplifier for amplifying an output voltage of said Galvanic cell type oxygen sensor;
   an attenuator comprising resistors and switches connected to each other for attenuating an output signal from said operational amplifier;
   a switch control circuit for controlling the operation of said switches by outputting a binary code;
   a first comparator for comparing an output signal from said attenuator with a first reference voltage and for determining whether or not said binary code from said switch control circuit is to be sequentially changed, said binary code being changed when said output signal from said attenuator is at a first value with respect to said first reference voltage; and,
   a second comparator for comparing said output signal from said attenuator with a second reference voltage and for activating an alarm when said output signal from said attenuator is at a second value with respect to said second reference voltage,
   wherein the maximum output of said Galvanic cell type oxygen sensor is determined by said switch control circuit and said attenuator, and calibration is automatically conducted such that said maximum output of said Galvanic cell type oxygen sensor corresponds to an oxygen concentration of 21%, and when an oxygen concentration, corresponding to said output signal from said attenuator, becomes lower than a predetermined value, corresponding to said second reference voltage, said alarm is activated.

2. An oxygen concentration monitor as claimed claim 1, wherein said first value is greater than said first reference voltage and said second value is lower than said second reference voltage.

3. An oxygen concentration monitor comprising:
   a Galvanic cell type oxygen sensor;
   an attenuator comprising resistors and switches connected to each other for attenuating an output voltage of said Galvanic cell type oxygen sensor;
   an operational amplifier for amplifying the output of said attenuator;
   a switch control circuit for controlling the operation of said switches by outputting a binary code;
   a first comparator for comparing an output signal from said operational amplifier with a first reference voltage, and for determining whether or not said binary code from said switch control circuit is to be sequentially changed, said binary code being changed when said output signal of said operational smplifier is at a first value with respect to said first reference voltage; and,
   a second comparator for comparing said output signal from said operational amplifier with a second reference voltage and for activating an alarm when said output signal from said operational amplifier is at a second value with respect to said second reference voltage,
   wherein the maximum output of said Galvanic cell type oxygen sensor is determined by said switch control circuit and said attenuator and calibration is automatically conducted such that said maximum output of said Galvanic cell type oxygen sensor corresponds to an oxygen concentration of 21%, and when an oxygen concentration, corresponding to said output signal from said attenuator, becomes lower than a predetermined value, corresponding to said second reference voltage, said alarm is activated.

4. An oxygen concentration monitor as claimed claim 3, wherein said first value is greater than said first reference voltage and said second value is lower than said second reference voltage.

5. An oxygen concentration alarm comprising:

a Galvanic cell type oxygen sensor;

an operational amplifier for amplifying an output of said Galvanic cell type oxygen sensor;

a feedback resistor comprising resistors and switches connected to each other for varying an amplifier gain of said operational amplifier;

a switch control circuit for controlling the operation of said switches by outputting a binary code;

a first comparator for comparing an output from said operational amplifier with a first reference voltage, and for determining whether or not said binary code from said switch control circuit is to be sequentially changed, said binary code being changed when said output signal of said operational amplifier is at a first value with respect to said first reference voltage; and, a second comparator for comparing said output from said operational amplifier with a second reference voltage, and for activating an alarm when said output from said operational amplifier is at a second value with respect to said second reference voltage, wherein the maximum output of said Galvanic cell type oxygen sensor is determined by said switch control circuit and said feedback resistor, and calibration is automatically conducted such that said maximum output of said Galvanic cell type oxygen sensor corresponds to an oxygen concentration of 21%, and when an oxygen concentration, corresponding to said output signal from said operational amplifier, becomes lower than a predetermined value, corresponding to said second reference voltage, said alarm is activated.

6. An oxygen concentration monitor as claimed claim 5, wherein said first value is greater than said first reference voltage and said second value is lower than said second reference voltage.

* * * * *